United States Patent

Bornstein et al.

[11] Patent Number: 6,099,310
[45] Date of Patent: Aug. 8, 2000

[54] DENTAL INSTRUMENT

[75] Inventors: Rolf Bornstein, Stockholm; Dan Ericson, Malmö, both of Sweden

[73] Assignee: MediTeam Dentalutveckling I Goteborg AB, Savedalen, Sweden

[21] Appl. No.: 09/331,208
[22] PCT Filed: Dec. 16, 1997
[86] PCT No.: PCT/SE97/02102
  § 371 Date: Jun. 17, 1999
  § 102(e) Date: Jun. 17, 1999
[87] PCT Pub. No.: WO98/29053
  PCT Pub. Date: Jul. 9, 1998

[30] Foreign Application Priority Data

Dec. 17, 1996 [SE] Sweden .................................. 9604626

[51] Int. Cl.[7] .................................................. A61C 3/00
[52] U.S. Cl. .................. 433/141; 433/143; 15/236.05
[58] Field of Search ..................... 433/141, 142, 433/143, 144, 165; 30/172; 15/236.01, 236.05, 236.06, 236.07, 236.09

[56] References Cited

U.S. PATENT DOCUMENTS

| | | | |
|---|---|---|---|
| Re. 11,118 | 10/1890 | Browne | 433/165 |
| 774,253 | 11/1904 | Keefe | 433/142 |
| 1,833,555 | 11/1931 | Bell et al. | 433/142 |
| 1,953,584 | 4/1934 | Bronner | 433/143 |
| 2,359,607 | 10/1944 | Bashara . | |
| 2,557,134 | 5/1951 | Berliner | 433/143 |
| 3,267,506 | 8/1966 | Van Patten . | |
| 3,943,628 | 3/1976 | Kronman et al. | 32/40 R |
| 4,270,902 | 6/1981 | Wiland | 433/143 |
| 4,793,807 | 12/1988 | Friedman et al. | 433/80 |
| 4,913,133 | 4/1990 | Tichy | 433/142 |
| 5,077,897 | 1/1992 | Jubran et al. | 30/172 |
| 5,388,989 | 2/1995 | Kountis | 433/143 |
| 5,743,737 | 4/1998 | Hawn et al. | 433/141 |

FOREIGN PATENT DOCUMENTS

| | | | |
|---|---|---|---|
| 0 398 893 B1 | 10/1993 | European Pat. Off. . | |
| 3103349 | 8/1982 | Germany | 433/142 |

*Primary Examiner*—Ralph A. Lewis
*Attorney, Agent, or Firm*—Pollock, Vande Sande & Amernick

[57] ABSTRACT

The invention relates to a dental instrument for removing carious dentine in connection with chemical-mechanical treatment of caries by means of a caries-dissolving solution applied to the caries for loosening the carious tissue. The instrument comprises at least one non-rotating tool-head (4, 5) for manually scraping away the loosened carious dental material. The tool head is star-shaped with a number of scraping edges (6) having a curved outer contour (periphery) for excavating loosened carious dental material in connection with said treatment method. The scraping edges (6) are designed to scrape in different directions, the bottom parts as well as the sides (peripheral parts) of a tooth cavity. The open spaces (9) formed between the scraping edges (6) admit transport by the instrument of drops of the solution used for the chemical-mechanical treatment method up to the carious tooth site.

6 Claims, 2 Drawing Sheets

DENTAL INSTRUMENT

BACKGROUND OF THE INVENTION

The present invention relates to a dental instrument for removing caries attacked dentine.

In traditional caries treatment the attacked tooth substance is removed mechanically by means of a dentist's drill or a cutting excavator. Such a caries treatment is often a painful and unpleasant experience for the patient. Some of the patients feel so uncomfortable with the treatment that they wait far too long before they visit a dentist, which means that it is often too late to save the caries attacked teeth. Extraction of the teeth is then the only treatment method that is left.

However, there are other methods which are based on a chemical-mechanical treatment for the removal of the caries attacked substance. A method of this type is described in SE 460258. According to this method a two-component liquid is mixed and then immediately applied on the caries site. Functioning in a biological way, the liquid makes the caries attacked substance soft without causing any damage to the tooth or the soft tissue. After 10–15 seconds the dentist can start removing the carious substance by means of an excavator. The excavating operation continues until all caries substance has been removed. Then the cavity is filled with a suitable material.

According to the above patent the two-component liquid consists of a sodium hypochlorite component and a nitrogen-containing component. The nitrogen-containing component consists of three nitrogen-containing compounds with different charge states; one neutral, one with a negative net charge and one with a positive net charge.

Unlike conventional mechanical caries treatment methods the biological treatment method is usually not at all painful. Neither does it require any investments in expensive equipments. It only requires an excavator instrument to remove softened carious dentine material.

Traditional excavator instruments, however, are not suitable for this purpose as they are cutting tools and not made for just scraping away already softened dentine material from different types of cavities and therefore could damage healthy dentine.

The specific instruments that have been previously used in connection with the chemical-mechanical treatment method are mainly related to the distribution of the liquid solution for softening the carious dentine material. An apparatus for supplying such a liquid is previously disclosed in U.S. Pat. No. 4,793,807. The apparatus comprises an applicator 34 having a tubular implement through which the solution is applied on the caries site. According to the patent specification the tubular implement has a spoon-shaped tip end 188 which can be used for removing by scraping carious dentine material. However, such an instrument with an applicator integrated scraping implement requires expensive equipment and is not suitable for practical, frequent, manual use. Furthermore, the tip ends are not designed for all kind of cavities.

SUMMARY OF THE INVENTION

An object of this invention is to provide a non-rotating hand-held instrument which scrapes in different directions and which has scraping edges adapted to all types of caries attacks.

A further object of the invention is to provide an instrument that can be used for catching and carrying drops of the fluid used for the chemical-mechanical treatment method up to the caries site.

According to the invention the instrument comprises at least one star-shaped tool head having a number of scraping edges with a curved outer contour (periphery) for scraping away loosened caries tissue, the scraping edges being designed to scrape in different directions the bottom parts as well as the sides of said cavities.

According to a preferred embodiment the instrument comprises two tool members being inclined with respect to an intermediate grip member, at least one of the tool members having a star-shaped tool head.

According a further preferred embodiment the star-shaped tool head comprises four symmetrically arranged scraping edges which together form a substantially spherical outer contour for the tool head.

BRIEF DESCRIPTION OF THE FIGURES

In the following an example of an instrument according to the invention will be described more in detail with reference to the accompanying drawings, wherein.

DETAILED DESCRIPTION OF INVENTION

Figure 1:
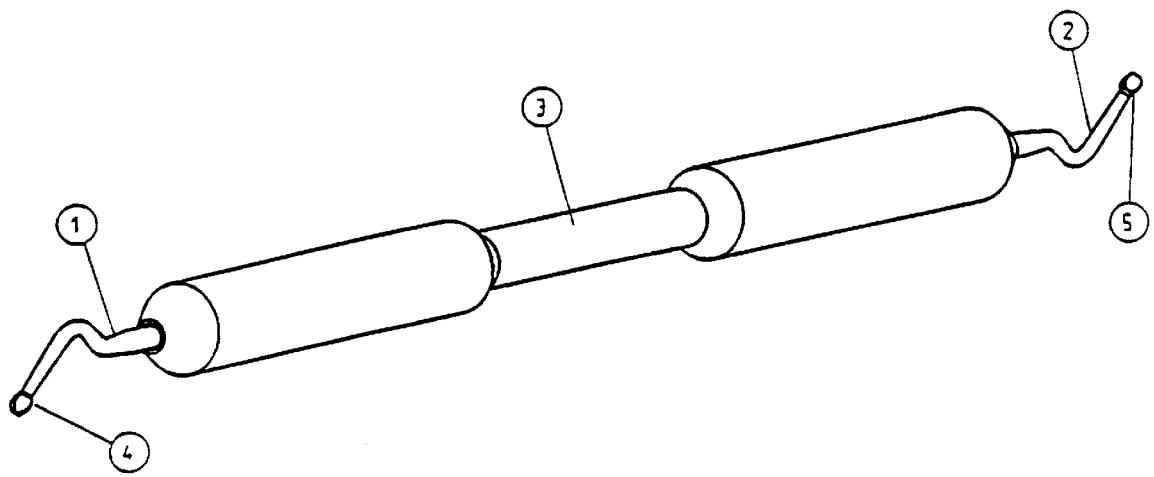
FIG. 1 is an overall view of the instrument.

As illustrated in FIG. 1 the instrument generally comprises two tool members 1,2 with a grip member 3 located between the tool members. The outer part of the two tool members are inclined to facilitate the use of the instrument in the mouth of a patient. This general design of the instrument is known and has been used for other applications.

However, the instrument has a new design with respect to the two tool heads 4,5 with the scraping edges. In the example illustrated here the two tool heads are star-shaped with a spherical outer contour. As an alternative one of the tool heads could be chisel-shaped. Such a chisel-shaped tip end, however, is traditional and will not be described here.

Figure 2:
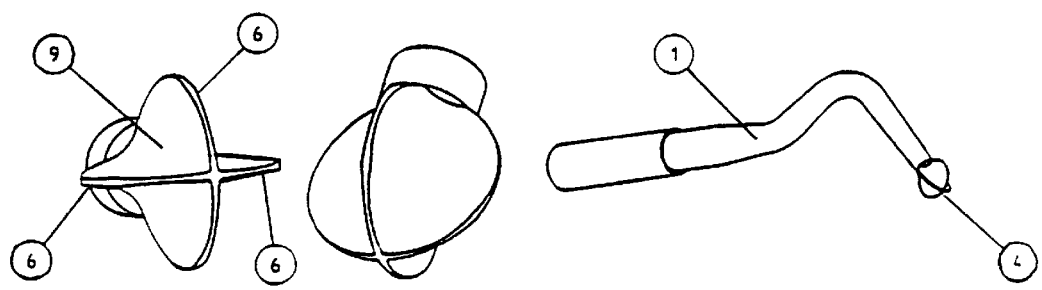
FIG. 2 illustrates the star-shaped tool head more in detail.

The star-shaped tool heads are specifically designed for scraping a cavity remaining in the tooth after a chemical (biological) treatment of a carious attack. The star-shaped tool head comprises four symmetrically arranged scraping edges 6 having a circular periphery, see FIGS. 2 and 3. The scraping edges 6 are extending outwardly in four different directions and due to the circular periphery the bottom parts as well as the sides of a cavity can be scraped with one and the same star-shaped tool head.

The star-shaped tool head can have less or more than four symmetrically arranged scraping edges. However, a common feature for the different embodiments is that each edge 6 has a substantially circular or curved outer peripheral edge so that the tool head can work on the bottom as well as along the sides (periphery) of the cavity.

Figure 3:
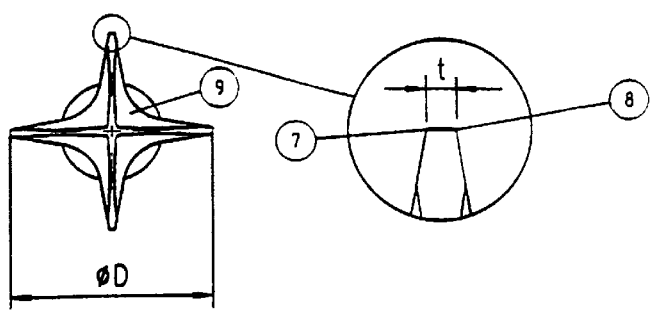
FIG. 3 is an axial view of the star-shaped tool head including a magnified view of one of the scraping edges.

As illustrated by the magnified view in FIG. 3 each of the scraping edges are tapered in the outward direction and they form a trapezoid section with two symmetrically arranged obtuse-angled corners 7, 8 providing the scraping function. So these obtuse-angled corners then have a scraping function instead of cutting like traditional instruments. As each of the edges has two symmetrically arranged scraping corners the scraping can be done in different directions. Preferably the instrument is handled by small whiskering movements so that it has a scraping function in different directions. The width t of the outer parts of the scraping edges is in this case approximately 0,1–0,5 mm, preferably 0,2 mm. The diameter D of the spherical tool head is preferably 1,0 to 3,0 mm.

Figure 4:
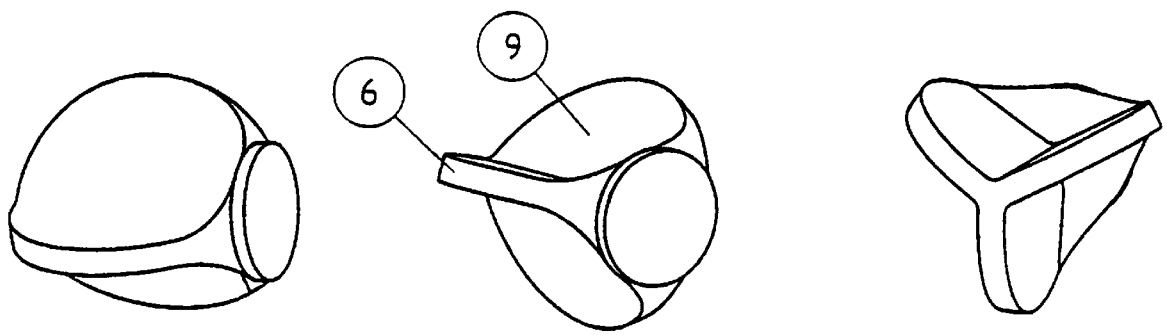
FIG. 4 illustrates some views of a slightly modified tool head.
Figure 5:
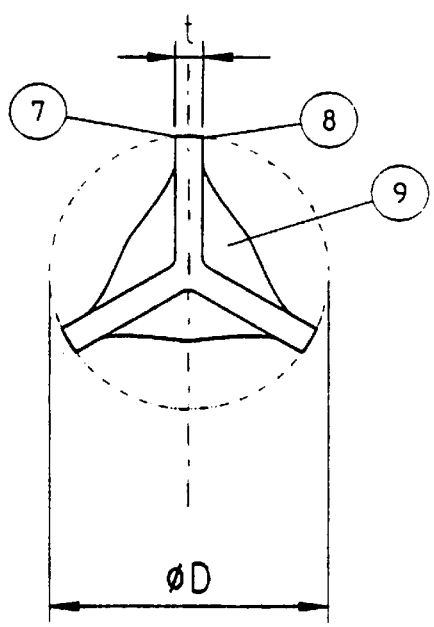
FIG. 5 is an axial view of said modified tool head.

In the example illustrated in FIG. 4 the star-shaped tool head also has a spherical outer contour, but in this case there are only three scraping edges 6 having a more rectangular cross-section with substantially parallel sides, i.e. not so tapered as the previously discussed embodiment. Also in this case the width t of the scraping edges is approximately 0,1–0,5 mm. And also in this case the scraping corners 7,8 are obtuse-angled in order to avoid cutting. The diameter D could be approximately 1,0 to 3,0 mm.

The open spaces 9 which are located between the scraping edges in both of the embodiments have a rounded design. These spaces 9 can be used for catching drops of the solution used for the chemical-mechanical caries treatment so that these drops are carried (transported) by the instrument up to the tooth in question. This function is specifically useful in case of a viscous (gel) substance. In this way the instrument also functions as a simple applicator for the viscous substance.

In the examples that have been discussed so far the star-shaped tool head has a substantially spherical outer contour. It should be understood, however, that other similar outer contours could also be used, such as oval shaped, elliptical, pear-shaped or the like. However, a common feture for all the different outer contours is that the scraping edges should be substantially curved, crescent-shaped (convex) so that the bottom parts as well as the side parts of the tooth cavity can be scraped without change of instrument or grip. Scraping edges with straight contours should not be used as they could damage healthy dentine.

The invention is not limited to the examples that have been illustrated here but could be varied within the scope of the accompanying patent claims.

What is claimed is:

1. Dental instrument for removing caries attacked dentine in connection with chemical-mechanical treatment of caries by means of a caries-dissolving solution applied to the caries for loosening the caries tissue, the instrument comprising at least one non-rotating tool head for manually scraping away the loosened caries tissue the tool head has a star-shaped cross-section with a number of scraping edges extending outwardly therefrom, the scraping edges having a curved outer contour scraping away loosened caries tissue, the scraping edges for the tool head being designed to scrape in different directions and being arranged to define open spaces therebetween, the open spaces being adapted for application of drops of the solution to the caries tissue.

2. Instrument according to claim 1 wherein the scraping edges have a spherical outer contour.

3. Instrument according to claim 1 wherein the tool head comprises four symmetrically arranged scraping edges.

4. Instrument according to claim 1 wherein the scraping edges are tapered radially in the outward direction and form a trapezoid section with two symmetrically arranged obtuse-angled corners providing the scraping function in different directions.

5. Instrument according to claim 4 wherein the outer parts of the scraping edges have a width of 0.1–0.5 mm and a diameter of the tool head is 1.0–3.0 mm.

6. Instrument according to claim 1 wherein the scraping edges extend radially from the tool head with substantially parallel sides and form a rectangular cross-section having two symmetrically arranged obtuse-angled corners for providing the scraping function in different directions.

* * * * *